United States Patent [19]

Dean et al.

[11] Patent Number: 4,490,303

[45] Date of Patent: Dec. 25, 1984

[54] IMINO ETHERS

[75] Inventors: Richard T. Dean, Fanwood; Conrad P. Dorn, Jr., Plainfield; Tsung-Ying Shen, Westfield, all of N.J.

[73] Assignee: Merck & Co., Inc., Rahway, N.J.

[21] Appl. No.: 421,751

[22] Filed: Sep. 23, 1982

Related U.S. Application Data

[62] Division of Ser. No. 270,422, Jun. 4, 1981, abandoned, which is a division of Ser. No. 145,173, Apr. 30, 1980, Pat. No. 4,304,720.

[51] Int. Cl.$^3$ .................... C07C 83/02; C07C 119/18
[52] U.S. Cl. ................................................ 260/453.99
[58] Field of Search ................................... 260/453.99

[56] References Cited

U.S. PATENT DOCUMENTS 3,115,513 12/1963 Stacey ........................... 260/453.99

Primary Examiner—Henry R. Jiles
Assistant Examiner—Robert C. Whittenbaugh
Attorney, Agent, or Firm—David L. Rose

[57] ABSTRACT

Fluorescein esters and ethers including the dioleyl derivative of fluorescein are disclosed. These compounds have the useful property of being fluorescent under the influence of the proper frequency of electromagnetic irradiation. Further, dioleyl fluorescein is readily incorporated into low-density lipoproteins which can then become part of the cell matter; the compounds retain their fluorescent properties during this procedure. The fluorescence allows cells to be indentified and separated. The fluorescein esters and ethers are prepared from fluorescein and the novel reagent O-alkenyl-N,N'-dialkylisourea.

7 Claims, No Drawings

IMINO ETHERS

This is a division of application Ser. No. 270,422, filed 6/4/81 now abandoned, which is a division of Ser. No. 145,173, filed 4/30/80, now U.S. Pat. No. 4,304,720, issued 12/8/81.

BACKGROUND OF THE INVENTION

Fluorescein is a known fluorescent agent; that is in the presence of ultraviolet light, solutions of the compound fluoresce, or give off light. This characteristic has been used to examine subterranian waters for sources of underground springs, and detecting sources of contamination of drinking water and infiltration with waste waters of factories. An extension of this use would be to have fluorescein incorporated into biological systems, such as cells to follow the paths of such cells, or to separate certain cells from other cells. However, this has not been possible owing to the nonincorporation or non-selective incorporation of fluorescein into such biological systems. The present invention solves this problem by providing means for incorporating fluorescein into cells, retaining the fluorescent qualities of the compound.

SUMMARY OF THE INVENTION

This invention concerns the ester and ether derivatives of fluorescein and procedures for preparing such compound from fluorescein and O-alkenyl-N,N'-dialkylisourea. Thus, it is an object of this invention to provide for such fluorescein derivatives. A further object is to describe the use of such fluorescein derivatives as fluorescent tracers to detect the presence of biological cells. A still further object is to provide for the preparation of such fluorescein derivatives. A still further object is to provide for the novel reagent used in the preparation of such fluorescein derivatives. Further objects will become apparent from a reading of the following description.

DESCRIPTION OF THE INVENTION

Fluorescein has the following structure:

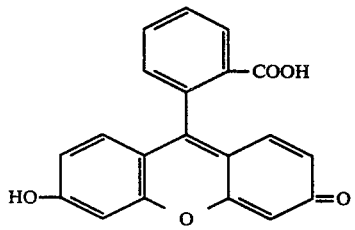

The compound of this invention, fluorescein esters and ethers have the following structure (I):

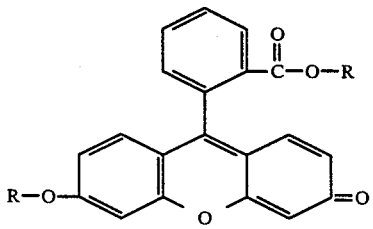

wherein R is an alkenyl group of from 12 to 30 carbon atoms and from 1 to 4 double bonds.

Examples of such alkenyl groups are lauroleyl ((Z)-9-dodecene), myristoleyl ((Z)-9-tetradecene), palmitoleyl ((Z)-9-hexadecene), oleyl ((Z)-9-octadecene), triacontyl ((Z)-9-triacontene), linoleyl ((Z,Z)-9,12-octadecadiene) linolenyl ((Z,Z,Z)-9,12,15-octadecatriene), eleostearyl (Z,Z,Z)-9,11,13-octadecatriene), arachidonyl ((Z,Z,Z,Z)-5,8,11,14-eicosatraenoic), and the like.

The preferred compounds of this invention are realized when the double bonds are all in a cis-configuration. Further preferred compounds are realized when there is one double bond in the alkenyl group. Still further preferred compounds are realized when the alkenyl group contains from 16 to 20 carbon atoms. The most preferred alkyl group contains 18 carbon atoms and is oleyl ((Z)-9-octadecene).

These compounds are prepared by reacting fluorescein with a reagent capable of alkylating the carboxylic acid as well as the phenolic hydroxyl groups. Common alkylating reagents known in the art for alkylating carboxylic acids and phenols were tried and found to be unsatisfactory. The novel reagent O-alkenyl-N,N'-dialkylisourea (II) was then prepared and this compound was found to successfully and simultaneously alkylate both the carboxylic acid and phenolic hydroxyls of fluorescein. The structure of this reagent is:

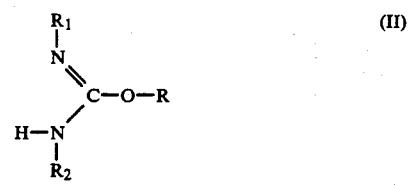

wherein R is as defined above and $R_1$ and $R_2$ are independently loweralkyl of from 1 to 6 carbon atoms or cycloalkyl of from 4 to 6 carbon atoms. The loweralkyl groups may be either straight or branched chain. The preferred compounds are those wherein $R_1$ and $R_2$ are the same. Further preferred compounds are when $R_1$ and $R_2$ are isopropyl or cyclohexyl. The most preferred compounds is when $R_1$ and $R_2$ are isopropyl.

The novel reagent of this invention (II) is prepared by reacting an N,N'-dialkyl-carbodiimide (III) with an alcohol (IV) as in the following reaction scheme:

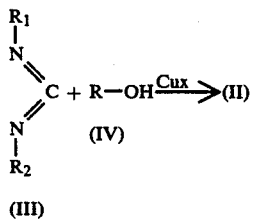

wherein R, $R_1$, and $R_2$ are as defined above.

Both starting materials are known in the art. In the reaction to prepare compound (II), the two compounds are combined in the presence of a cuprous halide (CuX). The cuprous halide, preferably cuprous chloride, is present in catalytic amounts. The reaction may be carried out in an inert aprotic solvent such as benzene, toluene, halogenated hydrocarbons and the like, however, it is preferred to combine the reactants without any solvent. The reaction is generally carried out using equimolar amounts of compounds III and IV, however, excesses of one reactant over the other has been found to be neither detrimental nor beneficial. Equimolar amounts are preferred, since this avoids removal of the excess reactant. The reaction is carried out at from room temperature to about 100° C. and is generally complete in from ½ to 24 hours. It is preferred to carry out the reaction at room temperature wherein the reaction has been found to be generally complete in about 3-5 hours. The product (II) is recovered from the reaction mixture using techniques known to those skilled in the art.

The products of this invention, ester and ether derivatives of fluorescein (I) are prepared by reacting fluorescein with the above prepared O-alkenyl-N,N'-dialkylisourea (II). Again, generally no solvent is used, or an inert solvent may be employed. Preferred solvents are dimethyl formamide, benzene, toluene, halogenated hydrocarbons, and the like. It is most preferred to carry out the reaction in dimethylformamide. The reaction is carried out at an elevated temperature of from 70°-200° C. Preferably from 90°-110° C. If a solvent is used with a boiling point less than the desired reaction temperature, a pressure bomb should be employed. The reaction is generally complete in from 2-48 hours. At the preferred temperature range, the reaction is generally complete in 5-18 hours. The reactants are generally used in substantially equimolar amounts or preferably with a slight excess of the O-alkenyl-N,N'-dialkylisourea.

The reaction has been found to alkenylate the carboxylic acid group and the phenolic hydroxyl group simultaneously and with equal facility under the above reaction conditions. This reaction may also be used to alkenylate other carboxylic acid groups and phenolic hydroxyl groups found on other biologically active molecules and, with the alkenyl function thereon, can be incorporated into the cells of biological systems.

The dialkenyl fluorescein finds utility in providing for the ready visualization of cells in biological systems and fluids.

The plasma lipoproteins are a family of globular particles each of which consists of a core of neutral lipid (primarily triglyceride or cholesteryl ester) surrounded by a coat of phospholipid and protein. One fraction of the plasma lipoprotein has been separated therefrom and is known as low-density lipoprotein (LDL). The LDL is the major cholesterol carrying lipoprotein of human plasma. The LDL attaches to the appropriate binding site of a cell and is drawn within the cell. The LDL coat is then ruptured and the contents of the core incorporated within the cell. Recently a method has been described by which the core of LDL is removed by extraction with heptane and replaced by exogenous cholesteryl esters. The LDL has retained its affinity for the cell binding site after this procedure and the exogenous cholesteryl esters have been incorporated into the cells.

It is thus realized that perhaps other exogenous materials could be placed into the LDL core to be eventually incorporated into a cell. The main barrier to this procedure is the requirement that the material to be placed in the LDL core be highly lipophilic.

In cell research, it is highly desirable to separate specific cells from a mixture of cells.

The instant procedure provides that cells may be visualized. Once cells are visualized, they may then be separated using techniques known to those skilled in the art.

Fluorescein is a highly fluorescent molecule and would readily aid in the identification and separation of cells, if it could be incorporated therein without affecting the cell. Unfortunately fluorescein is not at all lipophylic and, thus, cannot be incorporated into the cell via the LDL core transfer procedure. It has been found, however, that the alkenyl derivatives, particularly the dioleyl derivative of fluorescein is sufficiently lipophilic to be incorporated into the LDL core. In addition, the LDL with the dioleyl fluorescein core retains its affinity for the cell binding site and further, the cell, once it has ruptured the LDL coat and incorporated the dioleyl fluorescein therein, is highly fluorescent.

The fluorescent cells are, thus, easily visualized under visible or ultraviolet light and fractions of cells thus are readily separated. Generally, this is accomplished with a fluorescence activated cell sorter. In addition, it has been found that the fluorescent nature imparted to the cells does not affect the properties of such cells such that they may be used for whatever purposes the researcher intends without untoward effects.

The foregoing technique thus provides for an easily detected visual probe that can be used to determine whether or not a cell in a culture expresses LDL receptors. The use of fluorescent LDL also enhances the ease with which cells are screened for mutations in the LDL uptake pathway, including mutagens in patients with familial hypercholesterolemia as well as mutations that are created through in vitro mutagenesis in cultured cells.

The following examples are presented in order that the invention might be more fully understood. They are not to be construed as limitative of the invention.

EXAMPLE 1

O-Oleyl-N,N'-Diisopropylisourea

A mixture of N,N'-diisopropylcarbodiimide (12.6 g, 0.1 mole), oleyl alcohol (26.8 g, 0.1 mole) and cuprous chloride (60 mg) is stirred at room temperature for 4 hours. Infrared analysis shows the reaction to be virtually complete. The reaction mixture is placed on a column of alumina (454 g) and eluted with methylene chloride to give 36.2 g of O-oleyl-N,N'-diisopropylisourea. The product is identified by mass spectrometry (molecular ion at m/e 394), infrared spectroscopy (the C=N band at 1660 cm$^{-1}$) and nuclear magnetic resonance in deuterated chloroform; resonances are given in δ relative to tetramethylsilane: 0.9-2.2 (multiplet 37 protons); 2.9-3.8 (multiplet 3 protons); 4.0 (triplet, 2 protons) 5.3 (multiplet, 2 protons).

EXAMPLE 2

Dioleyl Fluorescein

A mixture of fluorescein (1.33 g, 4.0 mmole) and O-oleyl-N,N'-diisopropylisourea (3.48 g, 8.8 mmole) are heated under a blanket of nitrogen for 16 hours at 142° C. Analysis of an aliquot on a thin layer chromatography plate (silica gel eluting with 95% chloroform 5% methanol) indicates that all of the fluorescein is reacted. The residue is taken up in 100 ml. of ether, filtered and passed through 2.0 g of silica gel to give 3.91 g of crude material. The crude material is purified by preparative high pressure liquid chromatography using 325 g of silica gel on a Waters Associates System 500 instrument, at a flow rate of 200 ml per minute of a 4:1 mixture of methylene chloride and ether. The product, dioleyl fluorescein, separates with an Rf of 0.35. The product is identified by mass spectrometry (field desorption) with a single peak at M+H of 834; infrared spectroscopy (carbonyl absorption at 1720 cm$^{-1}$; nuclear magnetic resonance is deuterated chloroform; resonances are given in δ relative to tetramethylsilane: 0.9–2.2 (multiplet, 62 protons) 6.01 multiplet, 4 protons), 5.3 (multiplet, 4 protons) 6.4–8.3 (multiplet, 10 protons).

EXAMPLE 3

Following the procedure of Example 1 using N,N'-diisopropylcarbodiimide, cuprous chloride and the following alcohols:
   Lauroleyl alcohol
   Myristoleyl alcohol
   Palmitoleyl alcohol
   Triacontyl alcohol
   Linoleyl alcohol
   Linolenyl alcohol
   Eleostearyl alcohol
   Arachidonyl alcohol The following compounds are produced:
   O-Lauroleyl-N,N'-diisopropylisourea
   O-Myristoleyl-N,N'-diisopropylisourea
   O-Palmitoleyl-N,N'-diisopropylisourea
   O-Triacontyl-N,N'-diisopropylisourea
   O-Linoleyl-N,N'-diisopropylisourea
   O-Linolenyl-N,N'-diisopropylisourea
   O-Eleostearyl-N,N'-diisopropylisourea
   O-Arachidonyl-N,N'-diisopropylisourea

EXAMPLE 4

Following the procedure of Example 2, using fluorescein and the compounds prepared in Example 3, the following compounds are prepared:
   Dilauroleyl fluorescein
   Dimyristoleyl fluorescein
   Dipalmitleyl fluorescein
   Ditriacontyl fluorescein
   Dilinoleyl fluorescein
   Dilinolenyl fluorescein
   Dieleostearyl fluorescein
   Diarachidonyl fluorescein

What is claimed is:

1. A compound having the formula:

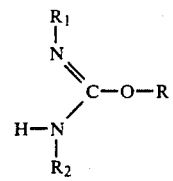

wherein R is an alkenyl group of from 12 to 30 carbon atoms with one double-bond in this cis configuration and R$^1$ and R$^2$ are independently loweralkyl of from 1 to 6 carbon atoms or cycloalkyl of 4 to 6 carbon atoms.

2. The compound of claim 1 wherein the R group contains from 16 to 20 carbon atoms.

3. The compound of claim 2 wherein the R group contains 18 carbon atoms.

4. The compound of claim 3 wherein the R group is oleyl.

5. The compound of claim 1 wherein R$_1$ and R$_2$ are the same.

6. The compound of claim 5 wherein R$_1$ and R$_2$ are isopropyl or cyclohexyl.

7. The compound of claim 6 wherein R$_1$ and R$_2$ are isopropyl.

* * * * *